United States Patent [19]

Fukunaga

[11] 4,005,091
[45] Jan. 25, 1977

[54] SUBSTITUTED TRIMETHYLENE CYCLOPROPANES, SALTS THEREOF, INTERMEDIATES AND METHODS OF MAKING THE SAME

[75] Inventor: Tadamichi Fukunaga, Hockessin, Del.

[73] Assignee: E. I. Du Pont de Nemours and Company, Wilmington, Del.

[22] Filed: Mar. 2, 1976

[21] Appl. No.: 663,101

Related U.S. Application Data

[62] Division of Ser. No. 535,138, Dec. 20, 1974, Pat. No. 3,963,769.

[52] U.S. Cl. .......................... 260/286 R; 260/295 S; 260/297 R; 260/468 H; 260/567.6 M; 260/586 R

[51] Int. Cl.$^2$ ......................................... C07C 49/61

[58] Field of Search ....... 260/468 H, 286 R, 295 S, 260/567.6 M, 586 R

[56] References Cited

OTHER PUBLICATIONS

Waitkus et al., J. Am. Chem. Soc., 1967, 89, pp. 6318–6327.

Yoshida et al., Topics in Current Chemistry, vol. 40 (1973) pp. 65–66.

*Primary Examiner*—Paul M. Coughlan, Jr.

[57] ABSTRACT

Trimethylenecyclopropane wherein all six hydrogen atoms are symmetrically substituted with cyano, alkoxycarbonyl or carbacyl groups and which are salt-forming can be made by reacting tetrachlorocyclopropene with the appropriate active methylene compound such as malononitrile, acetyl acetone or ethyl cyanoacetate. Using limited amounts of malononitrile and a tertiary amine, a tetracyanodimethylenecyclopropene substituted with a quaternary ammonium group is obtained, which reacts with other active methylene compounds including the above, nitroalkanes, benzoylacetonitrile, benzenesulfonylacetonitrile, and dialkyl sulfones to form unsymmetrical substituted trimethylenecyclopropane. The neutral compounds are useful as organic oxidants. Their radical anion salts are useful as organic conductors and as dyes, and the dianion salts are useful as image formers on transparent films or on opaque substrates.

15 Claims, No Drawings

SUBSTITUTED TRIMETHYLENE CYCLOPROPANES, SALTS THEREOF, INTERMEDIATES AND METHODS OF MAKING THE SAME

RELATIONSHIP TO OTHER APPLICATIONS

This application is a divisional application of copending application Ser. No. 535,138, filed Dec. 20, 1974, Pat. No. 3,963,769.

BACKGROUND OF THE INVENTION

1. Field of the Invention

The invention relates to novel negatively substituted trimethylenecyclopropanes, their radical anions and dianions, to intermediates therefore and to methods of making the same.

2. Prior Art

Trimethylenecyclopropane and its hexamethyl derivative have been reported by Waitkus et al. (J. Am. Chem. Soc. 1967, 89, 6318) and others (Kobrich et al., Tetrahedron 1967, 23, 565; Bleiholder & Shechter, J. Am. Chem. Soc. 1964, 86, 5032; Kobrich & Heinemann, Angew. Chem. 1965, 77, 590). Triquinocyclopropanes have been reported by West and Zecher (J. Am. Chem. Soc. 1967, 89, 152; 1970, 92, 149, 155). Triaminocyclopropenium ions and negatively substituted methylene (diamino) cyclopropenes derived from them have been reported by Yoshida et al. (J. Am. Chem. Soc. 1971, 93, 2573; Topics in Current Chemistry, Springer-Verlag, New York, Vol. 40, 1973, pp. 47–72).

SUMMARY OF THE INVENTION

The present invention comprises compounds of the formula

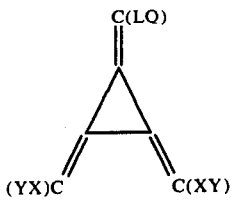

wherein X and Y are electron withdrawing groups selected from —CO (lower alkyl) or —COO (lower alkyl); and L and Q can be selected independently from —CO (lower alkyl) or —COO (lower alkyl) or pairwise from hydrogen and nitro; lower alkyl and nitro; hydrogen and lower alkyl sulfono; or lower alkyl and lower alkyl sulfono.

This invention also comprises salts $M^+Z^{\cdot -}$ and $M_2^+Z^{2-}$ wherein $Z^{\cdot -}$ is a radical anion formed by the addition of 1 electron, and $Z^{2-}$ is a dianion formed by the addition of two electrons to a compound of the above formula. $M^+$ is one equivalent of cation inert to the anions, preferably alkali metal ions, tetra(lower alkyl)ammonium ions, and pyridinium ions.

This invention also comprises intermediates for making the above compounds having the formula

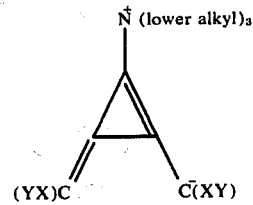

This invention further encompasses the method of making compounds of the formula

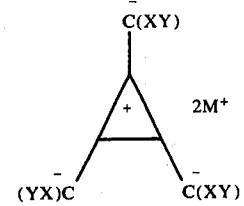

which comprises contacting and reacting, in an inert solvent, tetrachlorocyclopropene with a reagent of the formula $CH_2XY$ in the presence of a strong, non-nucleophilic base at a temperature in the range between −50° C. and 100° C.

This invention further comprises a method of making compounds of the formula

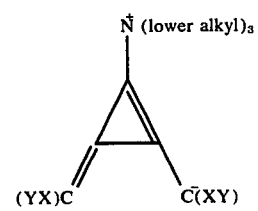

by contacting and reacting tetrachlorocyclopropene with $CH_2XY$ and N(lower alkyl)$_3$ in the molar ratios 1:2–3:5–6, at a temperature of −50° C. to 20° C. in an inert solvent.

Further, this invention comprises contacting and reacting

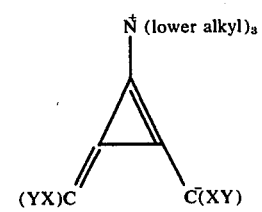

with the reagent $CH_2(LQ)$ in the presence of a strong, non-nucleophilic base, in the molar proportions 1:1–2:2–2.5 at a temperature in the range of 0° C. to 30° C. and in an inert solvent, to obtain compounds of the formula

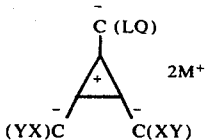

DETAILED DESCRIPTION OF THE INVENTION

The invention relates to a series of interrelated compounds and ions derived therefrom having the formulas:

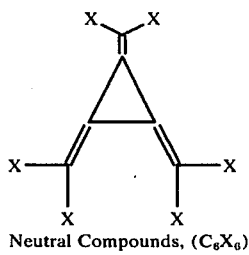

Neutral Compounds, (C$_6$X$_6$)

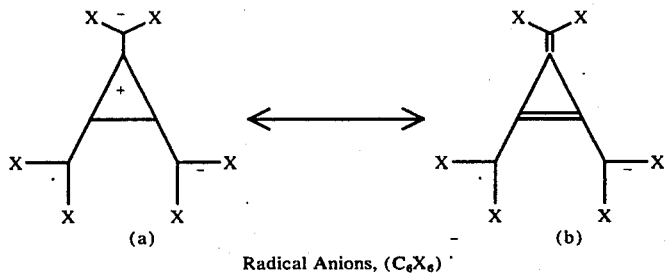

Radical Anions, (C$_6$X$_6$)$^-$

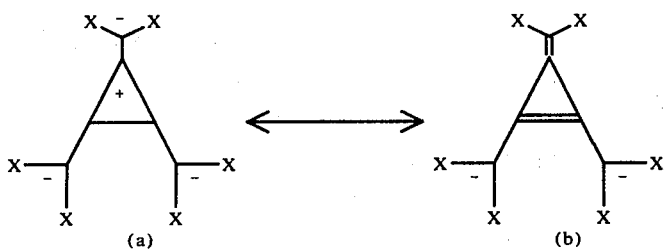

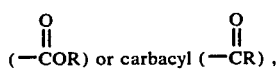

Dianions, (C$_6$X$_6$)$^=$

In the above formulas, each X can be cyano (-CH), alkoxycarbonyl $$(-\overset{O}{\underset{\|}{C}}OR) \text{ or carbacyl } (-\overset{O}{\underset{\|}{C}}R),$$

where R is lower alkyl, i.e., C$_1$—C$_6$ alkyl; or preferably when two methylene groups are substituted with four cyano, the remaining X's, respectively, are hydrogen and nitro (-NO$_2$); phenyl and cyano; phenylacetyl and cyano; or benzosulfonyl and cyano; hydrogen and lower alkyl sulfono; or lower alkyl and lower alkyl sulfono.

The neutral trimethylenecyclopropenes of formula I have strong oxidation power and, in many instances, are unstable in air or in solution, reverting rapidly to the radical anion form of formulas II-$a$ and II-$b$. Analytically pure samples can be held indefinitely only in the instance of hexa(methoxycarbonyl)trimethylenecyclopropane.

Certain radial anion compounds of formulas II-$a$ and II-$b$ are isolatable in the form of their salts, and all are generally detectable via polarographic half-wave potentials obtained during oxidation of the dianion form.

The dianion compounds of formulas III-$a$ and III-$b$ are readily insolatable in the form of their salts and in certain instances in the form of the conjugate diacids. The bis(tetrabutylammonium) [TBA] salts are especially useful for purification and characterization of the dianion species, and for their initial isolation.

Any cation inert to the anions can be employed to form salts including hydrogen ions, alkali metal ions, alkaline earth metal ions, tetra(lower alkyl) ammonium ions, pyridinium, quinolinium, tetrathiofulvalinium and like ions.

Ions which can exist in more than one value can be used to form salts of the radial anions or the dianion form provided that the redox potential of the cation is such that the selected anion is neither oxidized or reduced by the cation. The redox potentials of the dianions and anion radical species vary substantially with the substituents selected as shown by the Table I when the substituents are selected from cyano (CN) and methoxycarbonyl (COOCH$_3$) groups.

Table I

C(X$_1$, X$_2$)
(X$_6$, X$_5$)C   C(X$_3$, X$_4$)

| X$_1$ | X$_2$ | X$_3$ | X$_4$ | X$_5$ | X$_6$ | E$_1$ | E$_2$ |
|---|---|---|---|---|---|---|---|
| CN | CN | CN | CN | CN | CN | +0.34 | +1.13 |
| CN | CN | CN | CN | CN | E  | +0.26 | +1.0 |
| CN | CN | CN | CN | E  | E  | +0.11 | — |
| CN | CN | CN | E  | CN | E  | +0.17 | +0.97 |
| CN | E  | CN | E  | CN | E  | +0.10 | +0.72 |

Table I-continued $$\underset{(X_6, X_5)C \overset{\triangle}{\phantom{xx}} C(X_3, X_4)}{C(X_1, X_2)}$$

| $X_1$ | $X_2$ | $X_3$ | $X_4$ | $X_5$ | $X_6$ | $E_1$ | $E_2$ |
|---|---|---|---|---|---|---|---|
| CN | CN | E | E | E | E | +0.06 | +0.46 |
| CN | E | CN | E | E | E | +0.05 | +0.44 |
| CN | E | E | E | E | E | −0.01 | +0.32 |
| E | E | E | E | E | E | −0.07 | +0.16 |

Complex cations are also within the contemplation of this invention.

When the reaction to form the dianion compound is conducted with a strong base, the cation is ordinarily derived from the base, e.g., when sodium hydride, the preferred base is employed in non-aqueous solutions, the sodium salt of the dianion will be formed. However, other cations can be readily substituted by selection of the base or by conventional metathetical ionic reactions, e.g., crystallization of the dianion compound in the presence of an excess of a salt of the selected cation, by precipitation with certain salts such as tetrabutyl ammonium chloride since the tetrabutyl ammonium salts tend to be scarcely soluble in water; by the use of ion exchange resins or the like.

In this specification, the term "lower alkyl" refers to alkyl radicals, including branched alkyl radicals of up to six carbon atoms.

The interrelated compounds and ions of formulas I, II and III are prepared via the reaction of tetrachlorocyclopropene with appropriate active methylene compounds ($CH_2X_2$) in suitable single or stepwise procedures, depending upon the desired assortment and location of X substituents.

The single step method of preparing symmetrically substituted dianionic trimethylenecyclopropenes can be illustrated as follows, where X and Y, individually, are the strongly negative ($e^-$ withdrawing) groups CN, $CO_2R$ or COR, R being lower alkyl. Representative active methylene reactants are malononitrile, dimethyl malonate, dibutyl malonate, methyl cyanoacetate, hexyl cyanoacetate, acetylacetone, methyl acetoacetate, ethyl acetoacetate and acetylacetonitrile. The reaction proceeds with displacement of $Cl^-$ with $^-CHXY$ followed by deprotonation by excess base. The product may be conveniently isolated as an alkali metal or tetraalkylammonium salt, or as a conjugate acid released through protonation by a strong acid such as hydrochloric acid. In the original deprotonation, carried out in an anhydrous medium, sodium hydride is an effective and preferred base, but other strong nonnucleophilic bases can be used. In some instances a tertiary amine such as triethylamine is a suitable deprotonating base.

The reaction can be accomplished at temperatures in the range of about −50° to about +100°, preferably at a temperature in the range of 0°–25°. A preferred reaction medium is anhydrous 1,2-dimethoxyethane, and other suitable solvents are diethyl ether, dimethylformamide, hexamethylphosphoramide and dimethyl sulfoxide.

The bases employed are those which are known to be capable of abstracting active hydrogen atoms from the compounds containing active methylene groups which are employed, i.e., bases which are effective in such well-known reactions as the Dieckmann reaction, the Michael reaction, or like condensations with active methylene compounds.

The reaction can be conveniently conducted at atmospheric pressure, but other pressures can be employed if desirable.

The stepwise method of preparing negatively substituted trimethylenecyclopropanes involves the initial reaction of tetrachlorocyclopropene with a restricted amount of an appropriate active methylene compound together with an excess of a tertiary amine ($R_3N$, R being lower alkyl) as HCl scavenger. This method can be illustrated as follows:

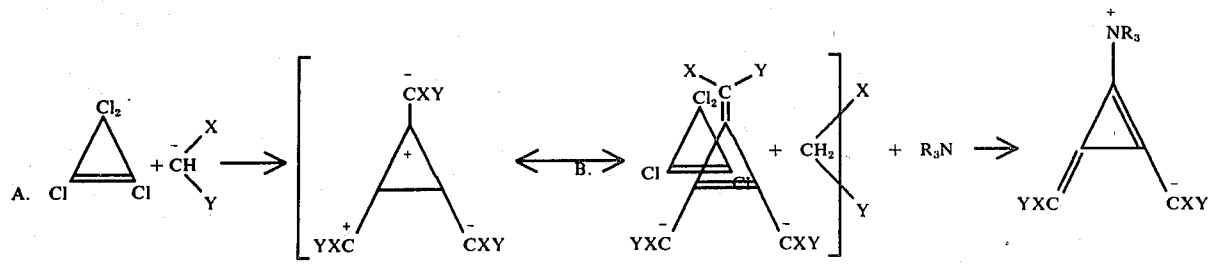

C. 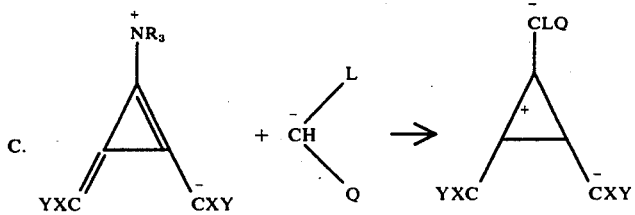

In reaction B the mole ratios of the three respective reactants is generally 1 to 2–3 to 5–6. If a large excess of $CH_2XY$ is used, a trimethylenecyclopropane can also be produced via reaction A. Triethylamine is a preferred tertiary amine. The reaction is carried out at a temperature in the range of −50° to +20°, and aprotic nonnucleophilic solvents such as chlorohydrocarbons (especially methylene chloride), diethyl ether, tetrahydrofuran, acetonitrile and dimethylformamide can be used. Ambient pressure is suitable and is preferred.

In reaction C the range of active methylene reactants ($CH_2LQ$) can be extended beyond that of the active methylene reactants ($CH_2XY$) usable in reaction A. Thus L and Q, individually, can be CN, COR or $CO_2R$, R being lower alkyl and the same or different to X and Y and, in pairs, can also be hydrogen or alkyl and nitro (as in nitromethane or nitroethane), phenyl and cyano (as in benzyl cyanide), benzoyl and cyano (as in benzoylacetonitrile), benzenesulfonyl and cyano (as in benzenesulfonylacetonitrile), or hydrogen or alkyl and alkylsulfono (as in dimethyl sulfone or diethyl sulfone). This reaction involves elimination of $NR_3$ and subsequent deprotonation by the base originally associated with $CHLQ^-$. A reaction temperature in the range from about 0° to about 30° is suitable; and slightly more than two equivalents of $CHLQ^-$ are generally used, but one equivalent of $CHLQ^-$ can be used in the presence of an additional equivalent of a base such as sodium hydride, or sodium methoxide. A combination of excess $CH_2LQ$ with $NR_3$ can also be employed. The product can be conveniently isolated as the bis(tetrabutylammonium) salt or, in some instances, as the conjugate diacid. Suitable solvents are alcohols, hexamethylphosphoramide, dimethylformamide, and dimethyl sulfoxide.

In procedures A and C the trimethylenecyclopropane product is obtained in the dianion form and is normally isolates as a salt, usually the bis-TBA salt. Formation of the radical ion and neutral forms requires oxidation, the existence of these generally unstable oxidized forms being readily observed via polarographic halfwave potentials. For oxidation to the radical ion form a persulfate, such as sodium or potassium persulfate, bromine, iodine, chlorine, N-bromo-, N-iodosuccinimide, and periodate are suitable oxidizing agents, and certain radical anion salts [e.g., of hexacyanotrimethylenecyclopropane, methoxycarbonylpentacyanotrimethylenecyclopropane and tris(methoxycarbonylcyanomethylene)cyclopropane] can be successfully isolated. Otherwise, presence of radial anions is clearly indicated by the formation of intensely colored (generally blue) solutions even if isolation of salts is not readily achieved. Formation of the neutral form, which is even more unstable in may instance than the radical anion form, can be achieved by means of oxidants such as persulfate ($S_2O_8^-$), bromine ($Br_2$), iodine ($I_2$), periodate ($IO_4^-$), and thallium [Tl(III)]. Characterization of the neutral form through isolation and conventional analysis has not proven easy and so far has been achieved completely only with hexa(methoxycarbonyl)trimethylenecyclopropane and partially with hexacyanotrimethylenecyclopropane.

The neutral compounds of the present invention are useful as oxidants. The radical anion salts are useful as electrical conductors and as dyestuffs for such fabrics as acetate acrylan, nylon, silk or wool, and the dianion salts are useful for photoimaging, and for printing.

Specific Embodiments

This invention is further illustrated by the following specific embodiments, which should not be construed as fully delineating the scope thereof.

EXAMPLE 1

Hexacyanotrimethylenecyclopropanediide

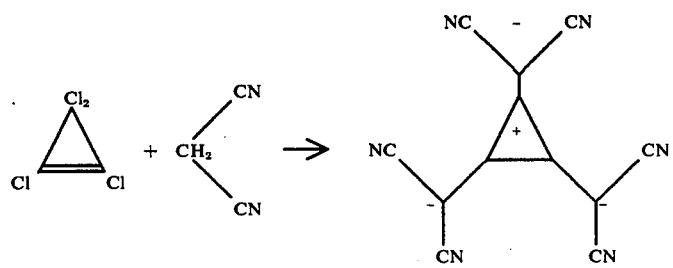

A. Tetrabutylammonium Salt

To a suspension of 45 g of 53% sodium hydride in 850 ml of anhydrous 1,2-dimethoxyethane (glyme) was added dropwise a solution of 30.0 g of malononitrile (purified by distillation) in 100 ml of anhydrous glyme at 0° over a 35-minute period. The mixture was stirred at 0° for 1 hour and a solution of 25 g of tetrachlorocyclopropene in 50 ml of anhydrous glyme was added dropwise at 0° over a 30-minute period. The yellow suspension was stirred at 0° for 1 hour and then decomposed carefully with water. The resulting mixture was dissolved in 500 ml of water and treated with a solution of 100 g of tetrabutylammonium bromide (TBABr) in 100 ml of water. The precipitated pale yellow solid was filtered, washed thoroughly with water and air-dried. A recrystallization from ethyl acetate:acetonitrile (3:1) gave 94.4 g (94%) of bis(tetrabutylammonium) hexacyanotrimethylenecyclopropanediide as colorless crystals; mp, 210°–213°.
Anal. Calcd for $C_{44}H_{72}N_8$: C, 74.11; H, 10.18; N, 15.71 Found: C, 74.14; H, 10.27; N, 16.17.
UV ($CH_3CN$): 315 nm ($\epsilon = 22,500$), 222 (35,800). IR (KBr): 4.57, 4.61, 7.05 $\mu$.
Oxidation potential ($CH_3CN$): +0.34, +1.13 V (vs SCE).

The TBA salt was also prepared from an isolated sample of the corresponding disodium salt (see Example 1-B) by treatment with TBABr in water.

B. Sodium Salt

To a suspension of 4.0 g of sodium hydride in 100 ml of anhydrous glyme was added a solution of 2.8 g of malononitrile in 10 ml of the same solvent at 0°. The mixture was stirred at 0° for 10 minutes and a solution of 2.5 g of tetrachlorocyclopropene in 10 ml of glyme was added dropwise at 0°. The yellow suspension was stirred at 0° for 1 hour and decomposed with 10 ml of saturated sodium chloride solution. The precipitated solid was filtered and recrystallized from 150 ml of water to give 2.7 g (71%) of disodium hexacyanotrimethylenecyclopropanediide as colorless solid.
Anal. Calcd for $Na_2C_{12}N_6$: C, 52.57; H, 30.65; Na, 16.77 for $Na_2C_{12}N_6 \cdot 1/3\ H_2O$: C, 51.44; N, 30.00; Na, 16.41 Found: C, 51.44; N, 30.76; Na, 16.21.
UV ($C_2H_5OH$): 315 nm ($\epsilon = 36,600$); 221 (41,300).
$C^{13}$-NMR [DMSO-$d_6$/Cr(Acac)$_3$]: 24.8, 121.0, 124.5 ppm (1:2:1)
Oxidation potential ($CH_3CN$): +0.34, +1.13 V (vs SCE)

The disodium salt was also obtained by treatment of the corresponding bis-TBA salt with excess sodium iodide in acetonitrile and by reaction of 1,2-bis(-dicyanomethylene)-3-triethylammoniumcyclopropanide (see Example 5) with sodio malononitrile.

The disodium salt was converted to the dipotassium salt by treatment with potassium iodide in hot water.

EXAMPLE 2

Tris-(methoxycarbonylcyanomethylene)cyclopropandiide

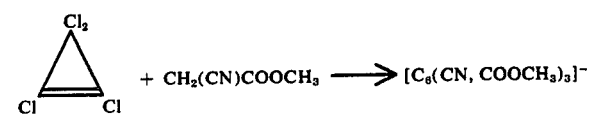

A. Bis(tetrabutylammonium) Salt

The title salt was prepared in the manner similar to that described in Example 1-A. The reaction mixture was evaporated under reduced pressure to dryness. The residue was dissolved in water, filtered, washed once with ether and treated with TBA bromide. The precipitated pale yellow solid was filtered and recrystallized from ethyl acetate containing a small amount of acetonitrile. From 10 g of tetrachlorocyclopropene and 18 g of methyl cycanoacetate there was obtained an 85% yield of the desired TBA salt, mp, 166°–170°, in two crops. An analytical sample, prepared by a further recrystallization from the same solvent mixture, was obtained as colorless crystals, mp, 168°–170°.
Anal. Calcd for $C_{47}H_{81}N_5O_6$: C, 69.50; H, 10.05; N, 8.62 Found: C, 68.80; H, 9.99; N, 8.21.
UV ($CH_3CN$): 328 nm ($\epsilon = 39,200$), 232 (32,300). IR (KBr): 4.60, 6.15, 7.09, 7.68, 8.54, 9.23 $\mu$. Oxidation potential ($CH_3CN$): +0.10, +.72 V (vs SCE).

B. Disodium Salt

Treatment of the above TBA salt with sodium iodide in acetonitrile gave the corresponding disodium salt, an aqueous solution of which reprecipitated the TBA salt on treatment with TBA bromide.

EXAMPLE 3

Hexa(methoxycarbonyl)trimethylenecyclopropandiide

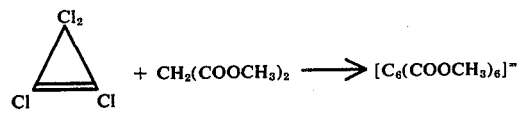

A. Conjugate Diacid

To a suspension of the sodium salt of dimethyl malonate, prepared from 16.5 g of 50% sodium hydride and 24 g of dimethyl malonate in 340 ml of anhydrous glyme, was added a solution of 10 g of tetrachlorocyclopropene in 20 ml of anhydrous glyme, dropwise at 0°–12°. The resulting thick yellow suspension was stirred at 20° for 1.5 hours, and the excess sodium hydride was decomposed by methanol. The yellow solid was collected by filtration and washed with methanol. The crude disodium salt was dissolved in water and acidified with 6N hydrochloric acid. The precipitated solid was filtered, washed with water, air-dried and recrystallized from carbon tetrachloride to give 13.7 g (57%) of the conjugate diacid of hexa(methoxycarbonyl)trimethylenecyclopropandiide as colorless crystals, mp, 121°–123°.
Anal. Calcd for $C_{18}H_{20}O_{12}$: C, 50.47; H, 4.71 Found: C, 50.60; H, 4.84.
UV ($CH_3CN$): 300 nm (sh) ($\epsilon = 2500$), 249 (22,400), 206 (11,400).
IR, (KBr): 5.31, 5.65, 5.75, 6.45, 6.95, 7.54, 7.95, 8.35, 9.28, 9.75 $\mu$.

B. Disodium Salt

The disodium salt was obtained as colorless powder either by treatment of the above conjugate diacid with sodium methoxide in methanol or by reduction of hexa(methoxycarbonyl)trimethylenecyclopropane (Example 20) by sodium iodide in acetonitrile.
Anal. Calcd for $Na_2C_{18}H_{18}O_{12} \cdot H_2O$: C, 44.09; H, 4.11 Found: C, 44.03; H, 4.53.
IR (KBr): 2.90, 5.95, 6.95, 7.40, 8.40, 9.02 $\mu$.

C. Bis(tetrabutylammonium) Salt

A solution of 1.0 mM of the above conjugate diacid in 20 ml of 0.1 M TBA hydroxide solution in benzene:-methanol (9:1) was evaporated. The oily residue was crystallized in ethyl acetate to give 818 mg (90%) of the bis(TBA) salt as colorless solid. An analytical sample was prepared by a recrystallization from ethyl acetate:acetonitrile (10:1), mp, 222.5 –224.5°.

Anal. Calcd for $C_{50}H_{90}N_2O_{12}$: C, 65.90, H, 9.96; N, 3.07 Found: C, 66.12; H, 10.01; N, 2.95.
UV ($CH_3CN$): 303 nm ($\epsilon = 38,600$), 267 (31,400).
IR (KBr): 5.90, 5.95, 7.07, 7.50, 8.48, 9.25 $\mu$.

D. Bis(tetramethylammonium) and Bis(tetraethylammonium) Salts

The conjugate diacid (one equivalent) was dissolved in two equivalents of 10% aqueous solution of tetramethylammonium hydroxide and likewise of tetraethylammonium hydroxide. The solutions were evaporated in vacuo and the residual oils were crystallized in ethyl acetate. Recrystallization from acetonitrile - ethyl acetate gave analytical samples. Bis(tetramethylammonium) Salt: mp 292°–295°
Anal. Calcd for $C_{26}H_{42}N_2O_{12}$: C, 54.34; H, 7.37; N, 4.88 Found: C, 54.44; H, 7.55; N, 4.98.

Bis(tetraethylammonium) Salt: mp 255–257°
Anal. Calcd for $C_{34}H_{58}N_2O_{12}$: C, 59.45; H, 8.51; N, 4.08 Found: C, 59.52; H, 8.64; N, 4.14.

EXAMPLE 4

Hexaacetyltrimethylenecyclopropandiide

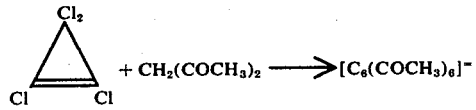

Conjugate Diacid

To a suspension of sodium acetylacetonate prepared from 8.5 g of 53.5% sodium hydride and 18.0 g of acetylacetone in 220 ml of anhydrous glyme was added a solution of 5.0 g of tetrachlorocyclopropene in 10 ml of anhydrous glyme at 0°. The resulting yellow suspension was stirred at 0° for 1 hour, diluted with water and washed once with methylene chloride. The aqueous solution was acidified with dilute hydrochloric acid and extracted with methylene chloride three times. The combined extracts were dried ($MgSO_4$) and evaporated. The residual solid was recrystallized from benzene to give 1.92 g (21%) of the conjugate diacid of hexaacetyltrimethylenecyclopropandiide as colorless crystals, mp, 158°–160°; mass spectrum, m/e 332.1261 (calcd for $C_{18}H_{20}O_{\mu}$, 332.1259); 222.0871 (calcd for $C_{12}H_{14}O_4$, 222.0891); 179:0702 (calcd for $C_{10}H_{11}O_3$, 179.0707).
Anal. Calcd for $C_{18}H_{20}O_6$: C, 65.05; H, 6.06 Found: C, 64.24; H, 5.93.

EXAMPLE 5

1,2-Bis(dicyanomethylene)-3-triethylammoniumcyclopropanide

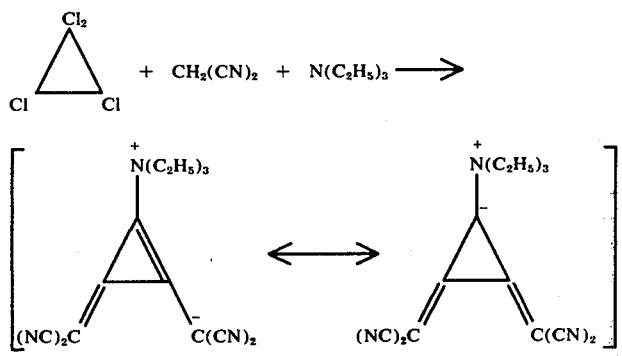

To a well stirred solution of 25 g of tetrachlorocyclopropene and 20 g of malononitrile in 650 ml of methylene chloride was added 80 g of triethylamine dropwise at −30°. The yellow mixture was slowly warmed to 0°, treated with 200 ml of water and filtered. The solid was successively washed with water, methanol and methylene chloride to give 32 g (86%) of the inner salt as slightly brownish solid. An analytical sample was prepared by a recrystallization from acetonitrile and obtained as colorless crystals: dec above 130°; mol weight (cryoscopic in DMSO), 263.
Anal. Calcd for $C_{15}H_{15}N_5$: C, 67.90; H, 5.70; N, 26.40 Found: C, 68.15; H, 5.75; N, 26.48.
UV ($CH_3CN$): 285 nm ($\epsilon = 32,600$).
IR (KBr): 4.50, 5.28, 6.55 $\mu$.

EXAMPLE 6

1,2-Bis[di(methoxycarbonyl)methylene]-3-triethylammoniumcyclopropanide

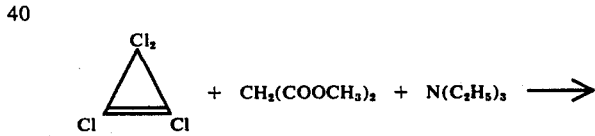

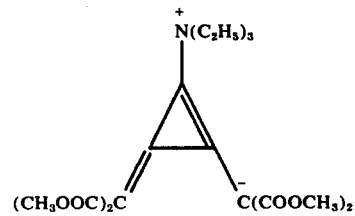

A solution of 25 g of tetrachlorocyclopropene and 41 g of dimethyl malonate in 600 ml of methylene chloride was treated with 77 g of triethylamine at −30°. The mixture was warmed to 0°, washed with water three times, and dried ($MgSO_4$). The solvent was evaporated and the residual solid was recrystallized from ethyl acetate to give 28 g (50%) of the desired inner salt as tan solid. An analytical sample, mp 185°–189° dec, was obtained as colorless crystals by a recrystallization from ethyl acetate.
Anal. Calcd for $C_{19}H_{27}NO_8$: C, 57.42; H, 6.85; N, 3.53 Found: C, 57.58; H, 6.86; N, 3.51.

UV (CH₃CN): 306 nm ($\mu$ = 35,200), 236 (15,400).
IR (KBr): 5.37, 5.88, 6.00, 6.70, 6.95, 7.55, 8.85, 9.15 $\mu$.

EXAMPLE 7

1,2-Bis(methoxycarbonylcyanomethylene)-3-triethylammoniumcyclopropanide

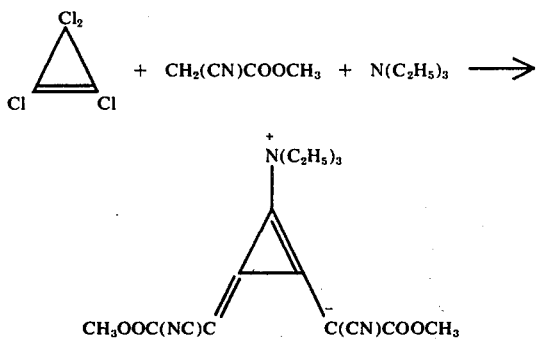

This inner salt was prepared in the manner similar to that described in Example 6. From 10 g of tetrachlorocyclopropene, 13 g of methyl cyanoacetate and 35 g of triethylamine there was obtained 15.2 g (82%) of the desired salt as tan solid. An analytical sample was obtained as colorless crystals, mp 227° dec (from 220° bath), by a recrystallization from acetonitrile. Anal. Calcd for C₁₇H₂₁N₃O₄: C, 61.62; H, 6.39; N, 12.69 Found: C, 61.71; H, 6.13; N, 12.80.
UV (CH₃CN): 297 nm ($\epsilon$ = 37,100), 235 sh (5980), 207 (23,600);
IR (KBr): 4.52, 5.33, 5.90, 6.75, 6.96, 7.74, 8.42, 9.00, 9.18 $\mu$.

EXAMPLE 8

Bis(dicyanomethylene)(methoxycarbobylcyanomethylene)cyclopropandiide

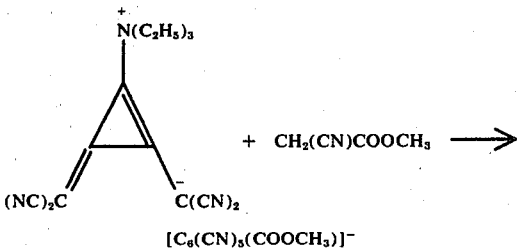

A. Bis(tetrabutylammonium) Salt

A solution of the sodium salt of methyl cyanoacetate was prepared from 6.0 g of sodium methoxide and 11.0 g of methyl cyanoacetate in 350 ml of methanol and treated with a solution of 13.5 g of the tetracyano inner salt (see Example 5) in 130 ml of hexamethylphosphoramide at 0° over a 1-hour period. The brown solution was stirred at 0° for 1 hour, then 60 g of TBA bromide was added. The methanol was evaporated under reduced pressure and the brown oily residue was allowed to stand at 20° overnight. The precipitated yellow solid, filtered and washed with ethyl acetate and water, weighed 27.7 g (73%). From the filtrate, a second crop (2.7 g) was obtained. Successive recrystallizations from ethyl acetate: acetonitrile and from dichloroethane gave an analytical sample of bis(tetrabutylammonium methoxycarbonylpentacyanotrimethylenecyclopropandiide as pale yellow prisms, mp, 209°-211°.
Anal. Calcd for C₄₅H₇₅N₇O₂: C, 72.44; H, 10.13; N, 13.14 Found: C, 72.26; H, 9.97; N, 13.06.
UV (CH₃CN): 322 nm ($\epsilon$ = 34,400), 224 (32,600).
IR (KBr): 4.59, 4.64, 6.10, 7.07, 7.61, 8.60, 9.20 $\mu$.
Oxidation potential (CH₃CN): +0.26, +1.0 V (vs SCE).

B. Disodium Salt

The above bis-TBA salt was converted to the disodium salt by treating it with sodium iodide in acetonitrile.

EXAMPLE 9

1,2-Bis(dicyanomethylene)-3-di(methoxycarbonyl)-methylenecyclopropandiide

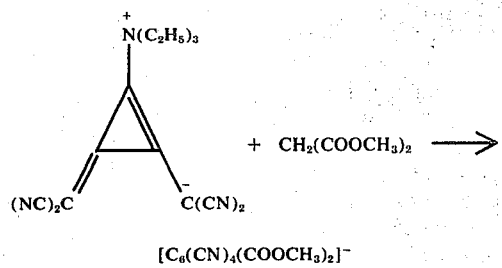

A. Bis(tetrabutylammonium)Salt

To a solution of sodio dimethyl malonate prepared from 1.5 g of 53.5% sodium hydride and 1.5 g of dimethyl malonate in 60 ml of anhydrous glyme was added a solution of 2.6 g of the tetracyano inner salt (Example 5) in 20 ml of hexamethylphosphoramide, dropwise at 0°. The brownish yellow mixture was stirred at 0° for 1.5 hours and then water was added to dissolve the precipitated yellow solid. The aqueous solution was washed once with methylene chloride, then treated with an aqueous solution of 10 g of TBA bromide. The precipitated yellow solid was filtered and recrystallized from ethyl acetate:acetonitrile to give 2.88 g (38%) of the bis-TBA salt as golden yellow crystals, mp, 234°-236°.
Anal. calcd for C₄₆H₇₀N₆O₄ : C, 70.91; H, 10.09; N, 10.79 Found: C, 70.81; H,10.27; N, 10.76.
UV (CH₃CN): 322 nm ($\epsilon$=32,800); 269 (17.200); 223 (27,600)
IR (KBr): 4.60, 4.65, 5.90, 6.22, 7.10, 7.50, 8.45, 9.00, 9.28 $\mu$
Oxidation potential (CH₃CH): 0.11 eV (vs SCE).

B. Disodium Salt

The above bis-TBA salt was treated with sodium iodide in acetonitrile to give the corresonding disodium salt as pale green tinted colorless solid.

EXAMPLE 10

1,2-Bis(methoxycarbonylcyanomethylene)-3-dicyanomethylenecyclopropandiide

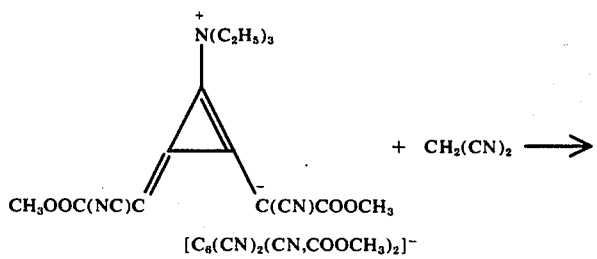

Bis(tetrabutylammonium) Salt

To a solution of sodio malononitrile prepared from 2.4 g of sodium methoxide and 2.9 g of malononitrile in 160 ml of methanol was added a solution of 6.4 g of the diester dicyano inner salt (Example 7) in 190 ml of hexamethylphosphoramide, dropwise at 0°. The reaction mixture was warmed to room temperature and stirred for 2.5 hours. The dark orange solution was treated with 30 g of TBA bromide and the methanol was evaporated. The residual solution was diluted with water to 700 ml and the precipitated yellow solid weighed 4.57 g (30.4%). A recrystallization from ethyl acetate:acetonitrile gave 4.13 g of the bis-TBA salt as yellow crystals; mp, 141°–143°.

Anal. Calcd for $C_{46}H_{78}N_6O_4$: C, 70.91; H, 10.09; N, 10.79 Found: C, 71.19; H, 9.92; N, 10.83.
UV ($CH_3CN$): 326 nm ($\epsilon$ = 25,400); 227 (30,000).
IR (KBr): 4.57, 4.63, 6.10, 7.08, 7.64, 8.55, 9.19 $\mu$.
Oxidation potential ($CH_3CN$): +0.17, +0.97 V (vs SCE).

EXAMPLE 11

1,2-Bis(methoxycarbonylcyanomethylene)-3-di(methoxycarbonyl)-methylenecyclopropandiide

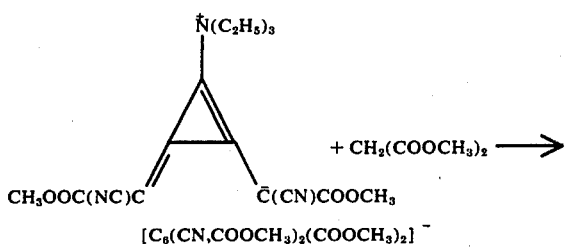

A. Monohydrogen Tetrabutylammonium Salt

A solution of sodio dimethyl malonate prepared from 2.4 g of sodium methoxide and 5.9 g of dimethyl malonate in 160 ml of methanol was treated dropwise with a solution of 6.7 g of the dicyanodimethoxycarbonyl inner salt (Example 7) in hexamethylphosphoramide at 0°–5°. The mixture was stirred at room temperature for 2 hours and then 30 g of TBA bromide was added. The methanol was evaporated, and the oily residue was diluted with water, acidified with 6N hydrochloric acid, and extracted with ethyl acetate three times. The combined extracts were washed with brine and dried (MgSO$_4$). The solvent was evaporated, and the residual solid was filtered and washed with ethyl acetate to give 8.2 g (68%) of colorless solid; mp, 104°–107°. A recrystallization from n-butyl chloride gave an analytical sample of the monohydrogen TBA salt as colorless crystals; mp, 113°–115°.

Anal. Calcd for $C_{32}H_{49}N_3O_8$: C, 63.66; H, 8.18; N, 6.96 Found: C, 63.56; H, 8.22; N, 7.08.
($CH_3CN$): 293 nm ($\epsilon$ = 40,900); 215 (sh) (19,800); 209 (20,600).
IR (KBr): 4,55, 5.35, 5,73, 5.76, 5.97, 6.04, 6.76, 7,00, 7,70, 8.60, 9.12 $\mu$.

B. Bis(tetrabutylammonium) Salt

A two-phase solution of 603 mg of the above salt (Example 11-A) in 10 ml of 0.1N TBA hydroxide solution in benzene:methanol (9:1) was evaporated and then taken up in ethyl acetate. The crystallized solid was filtered and recrystallized from ethyl acetate:acetonitrile to give 745 mg (88%) of the bis-TBA salt as colorless crystals; mp, 145.5°–147.0°.

Anal. Calcd for $C_{48}H_{84}N_4O_8$: C, 68.20; H, 10.01; N, 6.63 Found: C, 68,22; H, 9.88; N, 6.82.
UV ($CH_3CN$): 320 nm ($\epsilon$ = 34,600): 305 (sh) (31,900); 234 (25,400).
IR (KBr): 4.60, 5.85, 6.08, 6.71, 7.05, 7.12, 7.57, 7.65, 7.80, 8.40, 8.60, 9.30 $\mu$ Oxidation potential ($CH_3$ CN): +0.05, +0.44 V (vs SCE).

EXAMPLE 12

1,2-Bis[di(methoxycarbonyl)methylene]-3-dicyanomethylenecyclopropandiide

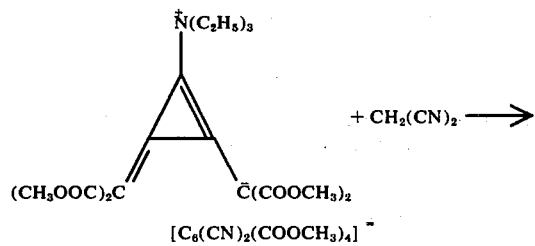

Bis(tetrabutylammonium) Salt

To a solution of sodio malononitrile prepared from 3.0 g of sodium methoxide and 3.7 g of malononitrile in 175 ml of methanol was added a solution of 10.0 g of the tetraester inner salt (Example 6) in 125 ml of methanol, dropwise at 0°. The dark brown solution was stirred at 0° for 2 hours, then 30 g of TBA bromide was added. The methanol was evaporated and the oily residue was disolved in water and extracted with methylene chloride three times. The combined extracts were dried (MgSO$_4$) and the solvent was evaporated. The residue was crystallized from ethyl acetate to give 8.62 g (40.5%) of the bis-TBA salt as yellow solid. A recrystallization from ethyl acetate:acetonitrile gave an analytical sample as colorless crystals; mp, 168°–171°.

Anal. Calcd for $C_{48}H_{84}N_2O_8$: C, 68.20; H, 10.02; N, 6.63 Found: C, 67.73; H, 10.28; N, 6.54.
UV ($CH_3CN$): 315 nm ($\epsilon$ = 32,000); 268 (22,700).
IR (KBr): 4.56, 4.62, 5.90, 7.00, 7.13, 7.50, 9.27, 11.33 $\mu$.
Oxidation potential ($CH_3CN$): +0.06, +0.46 V (vs SCE).

EXAMPLE 13

1,2-Bis[di(methoxycarbonyl)methylene]-3-methoxycarbonyl-cyanomethylenecyclopropandiide

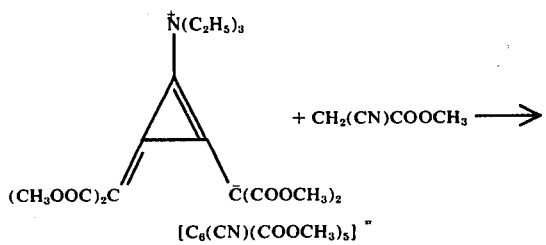

A. Bis(tetrabutylammonium) Salt

To a solution of sodio methyl cyanoacetate prepared from 3.0 g of sodium methoxide and 5.5 g of methyl cyanoacetate in 175 ml of methanol was added a solution of 8.5 g of the tetraester inner salt (Example 6) in 125 ml of methanol, dropwise at 0°. The solution was stirred at 0° for 2 hours and then 30 g of TBA bromide was added. The methanol was evaporated, the residue dissolved in 200 ml of water, and the aqueous solution extracted with methylene chloride. After drying (MgSO$_4$) the solvent was evaporated, and the solid residue was filtered and washed with ethyl acetate to give 12.8 g (68.7%) of the bis-TBA salt as colorless solid. The ethyl acetate filtrate was washed with water, dried (MgSO$_4$) and concentrated to give 2.8 g (20.9%) of the monohydrogen TBA salt (see Example 13-B).

The crude bis-TBA salt was recrystallized from ethyl acetate:acetonitrile to give colorless crystals; mp, 215°–218°.

Anal. Calcd for $C_{48}H_{87}N_3O_{10}$ : C, 67.01; H, 9.99; N, 4.79 Found: C, 66.80; H, 10.41; N, 4.84.

UV (CH$_3$CN): 315 (sh) nm ($\epsilon$ = 32,000); 299 (34,300); 238 (24,400).

IR (KBr): 4.60, 5.90, 7.02, 7.13, 7.52, 8.48, 9.2–9.3, 11.36 $\mu$.

Oxidation potential (CH$_3$CN): −0.01, +0.32 V (vs SCE).

B. Monohydrogen Tetrabutylamonium Salt

The title salt was obtained in Example 13-A, and also by treatment of the bis-TBA salt with dilute hydrochloric acid. A recrystallization from ethyl acetate gave an analytical sample as colorless crystals: mp, 145°–147°.

Anal. Calcd for $C_{33}H_{52}N_2O_{10}$ : C, 62.24; H, 8.23; N, 4.40 Found: C, 62.46; H, 8.56; N, 4.66.

UV (CH$_3$CN): 294 nm ($\epsilon$ = 43,700); 222 (16,400).

IR (KBr): 4.30, 5.37, 5.67, 5.85, 5.97, 7.00, 7.50, 7.80, 8.50, 9.05, 9.30 $\mu$.

EXAMPLE 14

1,2-Bis(dicyanomethylene)-3-nitromethylenecyclopropandiide

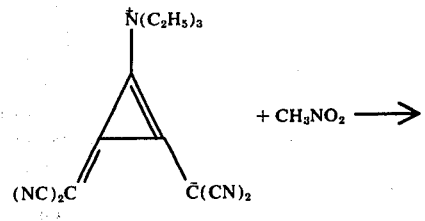

Bis(tetrabutylammonium) Salt

To a solution of 1.2 g of sodium methoxide in 60 ml of methanol was added a solution of 1.0 ml o nitromethane in 10 ml of methanol at 20°. The solution was cooled to 0° and a solution of 2.8 g of the tetracyano inner salt (Example 5) in 30 ml of hexamethylphosphoramide was added dropwise. The reaction mixture was stirred at 0° for 2 hours and then treated with an aqueous solution of 10 g of TBA bromide. The pecipitated solid was filtered, washed with water and air-dried to give 3.7 g of brown solid. A recrystallization from ethyl acetate gave 138 mg (2.8%) of the bis-TBA salt as yellow brown crystals; mp, 178°–180°.

Anal. Calcd for $C_{42}H_{73}N_7O_2$: C, 71.24; H, 10.39; N, 13.85 Found: C, 71.13; H, 10.62; N, 14.07.

EXAMPLE 15

1,2-Bis(dicyanomethylene)-3-($\alpha$-cyanobenzylidene) cyclopropandiide

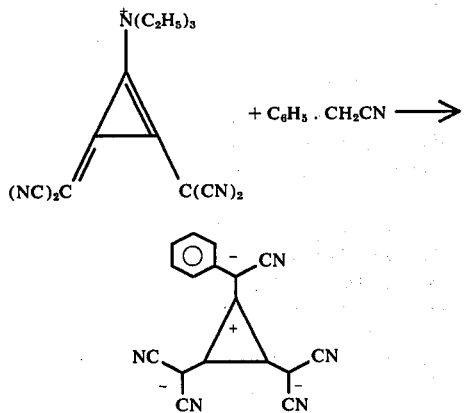

Bis(tetrabutylammonium Salt

To a solution of sodium methylsulfinylmethide prepared from 1.0 g of 50% sodium hydride and 20 ml of dimethyl sulfoxide was added a solution of 2.5 g of benzyl cyanide in 5 ml of dimethyl sulfoxide (DMSO) at 22°. After 30 minutes stirring at 22°, a solution of 2.7 g of the tetracyano inner salt (Example 5) in 20 ml of DMSO was added dropwise at 10°–20°. The dark brown mixture was stirred at room temperature, poured into ice water, treated with 10 g of TBA bromide and extracted three times with methylene chloride. The combined extracts were washed successively with water and saturated salt solution and dried (MgSO$_4$). The solvent was evaporated and the residual solid was recrystallized from ethyl acetate:acetonitrile to give 6.2 g (80%) of the bis-TBA salt as yellow solid. A recrystallization from ethyl acetate:acetonitrile (7:1) gave an analytical sample; mp, 139°–142° C.

Anal. Calcd for $C_{49}H_{77}N_7$: C, 77.01; H, 10.16; N, 12.83 Found: C, 76.99; H, 10.02; N, 12.75.

UV (CH$_3$CN): 372 nm ($\epsilon$=28,000), 323 (20,000), 279 (16,800), 238 (26,500).

IR (KBr): 4.62, 6.25, 6.70, 6.88, 7.10, 7.17, 8.50, 10.31, 11.35 $\mu$.

EXAMPLE 16

1,2-Bis(dicyanomethylene)-3-benzoylyanomethylenecyclopropandiide

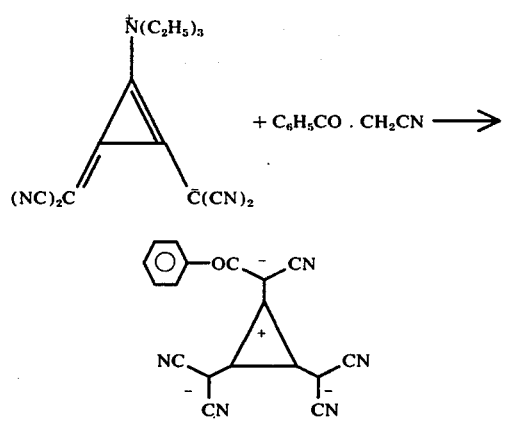

Bis(tetrabutylammonium) Salt

The title salt was prepared in the manner similar to that described in Example 15. After the reaction mixture had been poured into water and treated with TBA bromide, the mixture was stirred with ethyl acetate. The yellow solid was then filtered, washed with water and ethyl acetate and air-dried. From 3.1 g of benzoylacetonitrile and 2.7 g of the tetracyano inner salt, there was obtained 5.55 g (68.7%) of the bis-TBA salt; mp, 126°–128°.

Anal. Calcd for $C_{50}H_{77}N_7O$: C, 75.80; H, 9.80; N, 12.38 Found: C, 75.92; H, 10,00; N, 12.67.

UV ($CH_3CN$): 375 nm ($\epsilon$ = 15,100); 305 (22,300); 224 (33,000).

IR (KBr): 4.58, 6.28, 6.43, 7.05, 7.22, 7.45, 8.97, 11.27 $\mu$.

EXAMPLE 17

1,2-Bis(dicyanomethylene)-3-benzenesulfonyl-cyanomethylenecyclopropandiide

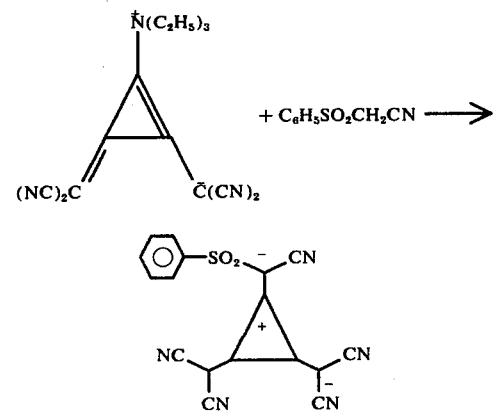

Bis(tetrabutylammonium) Salt

The title salt was prepared in the manner similar to that described in Example 16. From 1.0 g of 50% sodium hydride, 2.5 g of benzenesulfonylacetonitrile and 2.7 g of the tetracyano inner salt, there was obtained, after a recrystallization from ethyl acetate, 4.75 g of the desired TBA salt; mp, 145°–147°.

Anal. Calcd for $C_{49}H_{77}N_7SO_2$: C, 71.05; H, 9.37; N, 11.84; S, 3.87; Found: C, 70.94; H, 9.50; N, 12.14; S, 3.86.

UV ($CH_3OH$): 308 nm ($\epsilon$ = 25,800), 219 (29,700).

IR (KBr): 4,60; 7.10; 7.68, 8.47, 8.74, 9.18, 11.4, 13.85, 14.55 $\mu$.

EXAMPLE 18

Hexacyanotrimethylenecyclopropane Radical Anion

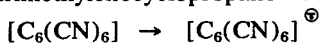

A. Bis(tetrathiafulvalene) Salt, $(C_6H_4S_4)_2 8C_6(CN)_6]$

To a solution of 119 mg of tetrathiafulvalene* monochloride (TTF Cl) in 150 ml of boiling ethanol was added a solution of 178 mg of the bis-TBA salt of hexacyanotrimethylenecyclopropandiide in 20 ml of hot ethanol. The mixture was allowed to stand at room temperature for six days, and then filtered to give 121 mg (75.6%) of $(TTF)_2[C_6(CN)_6]$ as black needlets; mp, 233°–234°.

Anal. Calcd for $C_{24}H_8N_6S_8$: C, 45.26; H, 1.27; N, 13.20 Found: C, 45.12; H, 1.29; N, 13.13.

Resistivity (compaction): 1 ohm cm.

UV ($CH_3CN$): 672 nm ($\epsilon$ = 15,000); 594 (14,400); 435 (20,700); 320 (43,700); 215 (35,000).

IR (KBr): 4.57, 7.00, 7.45, 8.90, 9.25 $\mu$.

*Coffen et al., J. Am. Chem. Soc. 1971, 93, 2258.

B. Potassium Salt

To a filtered solution of 15 g of potassium persulfate in 200 ml of warm water was added a solution of 7.275 g of the disodium salt of the hexacyanodianion (Example 1-B). The mixture was cooled, filtered, washed with water and dried in vacuo to give 6.653 g (94.5%) of potassium hexacyanotrimethylenecyclopropanide as reddish maroon crystals with copper-like luster. The radical anion salt does not melt but gives a burst of light on placing in a bath above 340°.

Anal. Calcd for $KC_{12}N_6$: C, 53.93; N, 31.45 Found: C, 53.79; N, 31.24.

UV ($CH_3CN$): 673 nm ($\epsilon$ = 19,900); 598 (12,900); 320 (30,500).

Resistivity (compaction): 3 × 10^5 ohm cm.

IR (KBr): 4.50, 6.70, 6.77 $\mu$.

A polarographic study confirmed the composition and showed no dianion. The esr spectrum showed, in addition to the $^{14}N$ isotropic hyperfine splitting (0.904G) and g value (2.00274), the splittings of 6.960, 9.945 and 1.29G due to $^{13}C$ of CN, $^{13}C$ of methylene carbons and $^{15}N$, respectively. No lines attributable to $^{13}C$ of ring carbons were detected.

C. Tris(dimethylamino)cyclopropenium Salt

To a hot filtered solution of 610 mg of tris(dimethylamino)cyclopropenium hexafluorophosphate in 125 ml of water was added a hot solution of 520 mg of potassium hexacyanotrimethylenecyclopropanide (Example 17-B) in 125 ml of water, through a fritted glass funnel. The still warm mixture was filtered and there was obtained 190 mg (24.6%) of the 1:1 complex as dark purple solid; mp, 162.5°–164.0°.

Anal. Calcd for $C_{21}H_{18}N_9$: C, 63.62; H, 4.58; N, 31.81 Found: C, 63.24; H, 4.53; N, 31.91.

Resistivity (compaction): 2 × 10^7 ohm cm.

UV ($CH_3CN$): 673 nm ($\epsilon$ = 18,900); 598 (12,400); 540 (sh) (6220); 322 (29, 500); 220 (38,600).

IR (KBr): 4.52, 5.49, 6.41, 7.10, 8.20, 9.60 μ.

D. Tetrabutylammonium Salt

A solution of 1.3 g of the dianion TBA salt in 30 ml of methylene chloride was treated with 0.1 ml of bromine. The blue solution was evaporated and the residue was taken up in water, filtered and washed with water to give 1.3 g of black solid. A recrystallization from 95% ethanol gave an analytical sample of the radical anion TBA salt as dark purple needles; mp, 124° dec. Anal. Calcd for $C_{28}H_{36}N_7$: C, 71.46; H, 7.71; N, 20.83 Found: C, 71.64; H, 7.75; N, 20.56.

Resistivity (compaction): $3 \times 10^8$ ohm cm.

Polarography ($CH_3CN$): all anion radical and no dianion.

UV ($CH_3CN$): 673 nm ($\epsilon = 19,300$), 598 (12,500), 320 (29,700), 215 (25,000).

IR (KBr): 4.51, 5.39, 6.72, 7.24, 11.28 μ.

E. Sodium Salts

A solution of 3.98 g of the dianion disodium salt in 70 ml of water was treated with 0.81 ml of bromine, filtered, and washed successively with water, alcohol and ether to give 2.73 g (73.6%) of $Na_6[C_6(CN)_6]_5$ as dark purple solid, which did not melt but gave a burst of light above 370°.

Anal. Calcd for $Na_6(C_{12}N_6)_5$: C, 56.31; N, 32.86 Found: C, 56.31; N, 33.25.

UV ($CH_3CN$): 673 nm ($\epsilon$ per $C_{12}N_6$ 20,000); 598 (13,000); 320 (30,700).

IR (KBr): 4.50, 6.70, 7.00 μ.

Polarography ($CH_3CN$): anion radical/dianion = $19 \pm 2/81 \pm 2$.

Resistivity (compaction): $3 \times 10^5$ ohm cm.

ESR (THF): 11 line pattern ($0.90 \pm 0.01$ G) (see Example 18-B).

The identical complex salt was obtained also from the dianion disodium salt and ferric chloride. Anal. Found: C, 56.19; N, 32.78.

A recrystallization from 95% ethanol gave the 3:2 salt, $Na_3[C_6(CN)_6]_2$, as blue solid; no melting and no high temperature flush.

Anal. Calcd for $Na_3(C_{12}N_6)_2$: C, 54.87; N, 32.00; Na, 13.13 Found: C, 54.61; N, 31.90; Na, 12.99.

UV ($CH_3CN$): 673 nm ($\epsilon$ per $C_{12}N_6$ 10,200); 598 (6600); 320 (31,000).

IR (KBr): 4.51, 4.58, 6.95 μ.

Polarography ($CH_3CN$): dianion/anion radical = $1.08 \pm 0.03$.

Resistivity (compaction): $1 \times 10^4$ ohm cm.

F. Pyridinium Salt

To a solution of 1.6 g of pyridinium bromide perbromide in 20 ml of methanol was added a solution of 1.35 g of disodium hexacyanotrimethylenecyclopropandiide in 35 ml of water. The mixture was cooled, filtered and washed with water, methanol and ether. The brown solid (1.153 g) was recrystallized from 95% ethanol to give 719 mg (46.7%) of the radical anion pyridinium salt as reddish maroon needles with metallic luster; mp, 203° dec (from 200° preheated bath).

Anal. Calcd for $C_{17}H_6N_7$: C, 66.23; H, 1.96; N, 31.81 Found: C, 66.17; H, 2.15; N, 30.62.

Resistivity (compaction): $1 \times 10^5$ ohm cm.

UV ($CH_3CN$): 673 nm ($\epsilon = 19,800$), 598 (12,700), 320 (30,300), 256 (7860), 224 (24,900).

IR (KBr): 4.51, 5.49, 6.10, 6.21, 6.50, 6.71, 11.35, 13.48, 14.95 μ.

G. Copper Salt

A solution of the dianion sodium salt was treated with cupric acetate (5 eq.) in water. There was obtained a blue solid (91%), which analyzed as $Cu_2[C_6(CN)_6]\cdot 2H_2O$. Anal. Calcd for $Cu_2C_{12}H_4N_6O_2$: C, 36.83; H, 1.03; N, 21.48 Found: C, 36.80; H, 0.90; N, 21.01. UV ($CH_3CN$) : 673 nm ($\epsilon > 11,600$); 598 ($>$ 7600); 320 ($>$ 23,800). IR (KBr): 2.90, 4.52, 7.00, 8.80 μ. Resistivity (compaction): $7 \times 10^5$ ohm cm.

EXAMPLE 19

Methoxycarbonylpentacyanotrimethylenecyclopropane Anion Radical

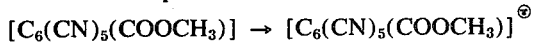

$[C_6(CN)_5(COOCH_3)] \rightarrow [C_6(CN)_5(COOCH_3)]^{\ominus}$

A. Potassium Salt

To a warm solution of 4.0 g of potassium persulfate in 60 ml of water was added a solution of 2.0 g of the disodium salt (Example 8-B) in 50 ml of warm water, through a fritted glass filter. The dark blue mixture was cooled in ice bath, filtered, washed with water and dried in vacuo at 80° to give 870 mg (44.6%) of the anion radical potassium salt hydrate as dark blue solid, which did not melt below 360°.

Anal. Calcd for $KC_{13}H_3N_5O_2 \cdot 2/3 H_2O$: C, 49.99; H, 1.40; N, 22.43 Found: C, 49.96; H, 1.37; N, 22.17.

Resistivity (compaction): $2 \times 10^6$ ohm cm.

UV ($CH_3CN$): 668 nm ($\epsilon = 18,100$); 592 (12,100); 325 (28,200); 218 (21,800).

B. Tetrathiafulvalene Salt

A hot solution of 119 mg of tetrathiafulvalene monochloride in 150 ml of ethanol was mixed with a hot solution of 187 mg of the bis-TBA salt of the pentacyanomonoester dianion (Example 8-A) in 20 ml of ethanol. The blue solution was allowed to stand at room temperature for 6 days. There was obtained 82 mg of the 1:1 complex as dark purple needlets; mp, 223°–224°.

Anal. Calcd for $C_{19}H_7N_5S_4O_2$: C, 49.01; H, 1.52; N, 15.04 Found: C, 49.04; H, 1.62; N, 15.37.

Resistivity (compaction): 100 ohm cm. UV ($CH_3CN$): 668 nm ($\epsilon = 19,300$); 590 (16,600); 435 (15,500); 325 (33,500); 217 (25,900).

EXAMPLE 20

Tris(methoxycarbonylcyanomethylene)cyclopropane Anion Radical

$[C_6(CN,COOCH_3)_3]^= \rightarrow [C_6(CN,COOCH_3)_3]^{\ominus}$

Potassium Salt

A solution of 3.7 g of the dianion disodium salt (Example 2-B) in 75 ml of water was added to a warm solution of 5.0 g of potassium persulfate and filtered immediately to give 3.16 g (86%) of the radical anion potassium salt as bright blue solid; mp, 270° dec.

Anal. Calcd for $KC_{15}H_9N_3O_6$: C, 49.17; H, 2.48; N, 11.47 Found: C, 48.71; H, 2.54; N, 11.59.

Resistivity (compaction): $2 \times 10^8$ ohm cm. UV ($CH_3CN$): 665 nm ($\epsilon > 6560$); 592 ($>$ 4730); 336 ($>$ 11,900); 223 ($>$ 9300).

EXAMPLE 21

Hexa(methoxycarbonyl)trimethylenecyclopropane

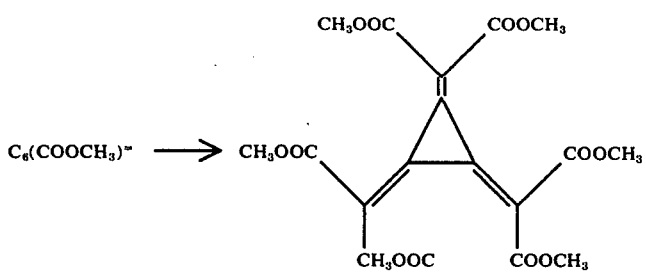

The conjugate diacid (2.0 g) of the hexaester dianion (Example 3-A) was added in portions into a stirred solution of 2.0 g of sodium periodate in 100 ml of water. Stirring was continued until the brown solid completely turned bright yellow. The solid was extracted with methylene chloride, dried ($MgSO_4$) and the solvent evaporated. The residue was taken up in ether, and the yellow solid was filtered and washed with ether to give 1.35 g of the hexaester. A recrystallization from n-butyl chloride afforded an analytical sample; mp, 137°–140°.
Anal. Calcd for $C_{18}H_{18}O_{12}$: C, 50.71; H, 4.26 Found: C, 51.03; H, 4.37.
Mass Spectrum: m/e 426.0805 (calcd for $C_{18}H_{18}O_{12}$; 426.0797).
NMR ($CDCl_3$): 3.90 ppm (s)
UV ($CH_3CN$): 400 (sh) nm ($\epsilon$ = 16,300); 375 (20,700); 223 (13,700).
IR (KBr): 3.36, 5.77, 6.95, 7.70, 8.1, 9.1, 9.6, 10.5, 12.1 $\mu$.
Reduction potentials ($CH_3CN$): −0.07, +0.022 V (vs SCE).

In some cases the crude oxidation product contained colorless solid insoluble in n-butyl chloride and benzene. Two recrystallizations from ethyl acetate:acetonitrile afforded colorless crystals; mp, 220°–230°, which are assigned the dimeric structure shown below.
Anal. Calcd for $C_{36}H_{38}O_{24}$: C, 50.59; H, 4.48 Found: C, 50.32; H, 4.45.
Mol. wt. (mass spec.): 854 (calcd: 854).
NMR ($CDCl_3$): 3.70 (s), 5.73 (s), (12:6:1).
UV ($CH_3CN$): 300 (sh) nm ($\epsilon$ = 4980); 254 (39,900); 206 (23,200).
IR (KBr): 5.31, 5.73 (br), 6.44, 6.95, 7.64, 7.95, 9.00, 9.35, 9.77, 11.20 $\mu$.

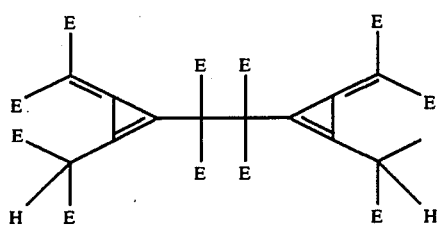

where E is $COOCH_3$.

EXAMPLE 22

Hexacyanotrimethylenecyclopropane

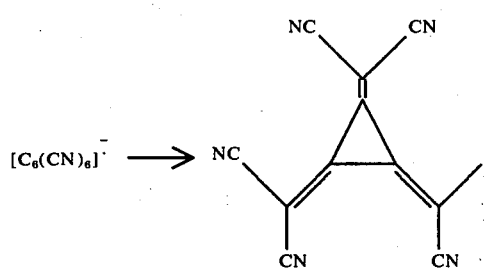

To a solution of 3.0 g of thallium(III) trifluoroacetate in 30 ml of trifluoroacetic acid and 5 ml of acetonitrile was added 1.0 g of $Na_6[C_6(CN)_6]_5$ (Example 17-E). The dark green mixture was stirred under argon. To dissolve blue solid, 40 ml of acetonitrile, 2.0 g of thallium (III) trifluoroacetate and 10 ml of trifluoroacetic acid were added in portions. The mixture was stirred for 6 hours and then filtered under argon to give 725 mg of hexacyanotrimethylenecyclopropane as tan solid, which turned brown in air, gave greenish-blue color in organic solvents and became dark below 250° without melting.
Mass Spectrum: m/e 228.0192 (calcd for $C_{12}N_6$: 228.0174), 176; 152.
IR (Nujol): 4.50, 6.41, 8.20, 9.43 $\mu$.

EXAMPLE 23

Photoimage Formation - Bis(tetrabutylammonium) Hexacyanotrimethylenecyclopropandiide Film prepared from a mixture consisting of 0.2 g of the title compound (Example 1-A), 5 ml of 10% solution of cellulose acetate butyrate in acetone, 0.2 g of 2,2'-bis(o-chlorophenyl-4,4',5,5'-tetraphenyl-bisimidazole, 0.5 g of 2,4-dichlorobenzaldehyde and 0.75 g of tricresyl phosphate was exposed to a sunlamp. Exposure to 100 $\mu$ joules/$cm^2$ light formed a blue image with 0.32 optical density.

EXAMPLE 24

Cloth Dye - Hexacyanotrimethylenecyclopropane Anion Radical

The potassium salt (Example 17) and the TBA salt (Example 17) gave blue or brown shades on acetate, acrylan, nylon, silk and wool.

EXAMPLE 25

Paper Printing - Bis(tetrabutylammonium) Hexacyanotrimethylenecyclopropandiide

A solution of the title compound (see Example 1-A) in acetonitrile was brushed on paper. The solvent evaporated in a few seconds. The residue was visible under a UV lamp, and showed a brilliant blue image after brief exposure to bromine vapor or a dilute solution of an oxidant such as N-bromosuccinimide.

What is claimed is:

1. A compound having the formula:

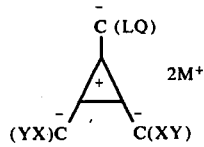

wherein X and Y are selected from —COO (lower alkyl) or —CO (lower alkyl); L and Q are independently selected from —COO (lower alkyl) or —CO (lower alkyl) or pairwise from —H and nitro, lower alkyl and nitro, hydrogen and lower alkyl sulfono, or lower alkyl and lower alkyl sulfono; and M+ is one equivalent of an inert cation.

2. A compound of claim 1 having the formula:

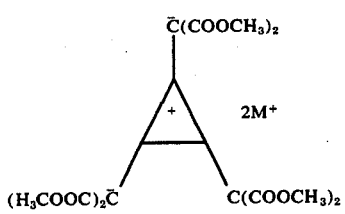

3. A compound having the formula:

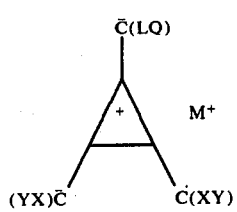

wherein X and Y are selected from —COO (lower alkyl) or —CO (lower alkyl); L and Q are independently selected from —COO (lower alkyl) or —CO (lower alkyl) or pairwise from —H and nitro, lower alkyl and nitro, hydrogen and lower alkyl sulfono, or lower alkyl and lower alkyl sulfono; and M+ is one equivalent of an inert cation.

4. A compound of claim 3 having the formula:

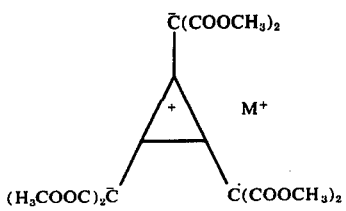

5. A compound having the formula:

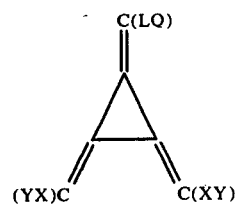

wherein X and Y are selected from —COO (lower alkyl) or —CO (lower alkyl); and L and Q are selected independently from —COO (lower alkyl) or —CO (lower alkyl) or pairwise from —H and nitro, lower alkyl and nitro, hydrogen and lower alkyl sulfono, or lower alkyl and lower alkyl sulfono.

6. A compound of claim 5 having the formula:

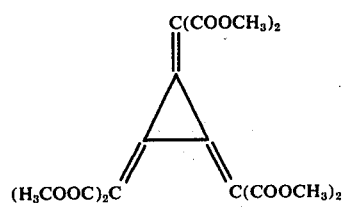

7. A compound of claim 5 having the formula:

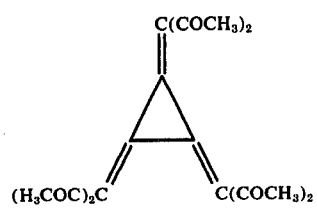

8. A compound having the formula:

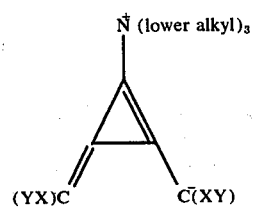

wherein X and Y are selected from —COO (lower alkyl) and —CO (lower alkyl).

9. A compound of claim 8 having the formula:

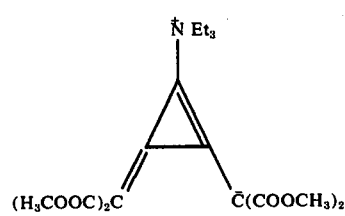

10. A method of making a compound having the formula:

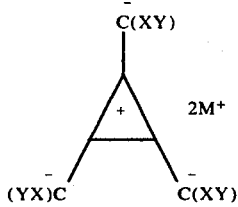

wherein X and Y are selected from —COO (lower alkyl) or —CO (lower alkyl) and M+ is one equivalent of an inert cation, which comprises contacting and reacting tetrachlorocyclopropene with $CH_2XY$ in the presence of a strong, non-nucleophilic base in an inert solvent, at a temperature of —50 to 100° C.

11. The method of claim 10 wherein the temperature is from 0° to 25° C.

12. The method of claim 10 wherein the base is sodium hydride.

13. A method of making a compound having the formula:

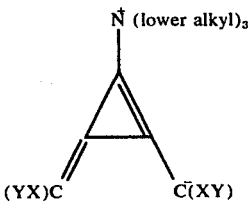

wherein X and Y are selected from —COO (lower alkyl) or —COO (lower alkyl) which comprises contacting and reacting tetrachlorocyclopropene with $CH_2XY$ and N(lower alkyl)$_3$ in the molar ratio 1:2–3:- 5–6 in an inert solvent, at a temperature of —50° to 20° C.

14. A method of making a compound having the formula:

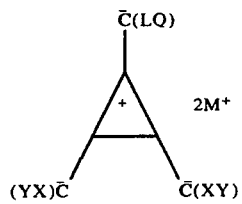

wherein X and Y are selected from —COO (lower alkyl) or —CO (lower alkyl); L and Q are independently selected from –COO(lower alkyl) or –CO (lower alkyl) or pairwise from –H and nitro, lower alkyl and nitro, hydrogen and lower alkyl sulfono, or lower alkyl and lower alkyl sulfono; and M+ is one equivalent of an inert cation, which comprises contacting and reacting

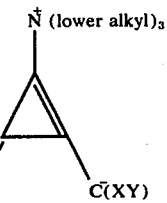

with $CH_2(LQ)$ and a strong, non-nucleophilic base in the molar proportions 1:1–2:2–2.5 in an inert solvent, at a temperature of 0° to 30° C.

15. The method of claim 14 wherein the base is sodium hydride.

* * * * *